United States Patent
Schmidt et al.

(10) Patent No.: US 7,360,399 B2
(45) Date of Patent: Apr. 22, 2008

(54) APPARATUS FOR MEASURING A DENSITY AND/OR A VISCOSITY OF A FLUID

(75) Inventors: Holger Schmidt, Kitzingen (DE); Wolfgang Drahm, Freising (DE); Hubert Koch, München (DE)

(73) Assignee: Endress + Hauser Flowtec AG, Reinach (CH)

( * ) Notice: Subject to any disclaimer, the term of this patent is extended or adjusted under 35 U.S.C. 154(b) by 171 days.

(21) Appl. No.: 11/104,476

(22) Filed: Apr. 13, 2005

(65) Prior Publication Data

US 2005/0284210 A1 Dec. 29, 2005

(30) Foreign Application Priority Data

Apr. 13, 2004 (DE) .................... 10 2004 018 326

(51) Int. Cl.
*G01N 9/32* (2006.01)
*G01N 11/02* (2006.01)
(52) U.S. Cl. ...................... 73/32 A; 73/54.41
(58) Field of Classification Search ............... 73/32 A, 73/54, 41, 61.44, 61.45, 61.49
See application file for complete search history.

(56) References Cited

U.S. PATENT DOCUMENTS

| | | | | |
|---|---|---|---|---|
| 4,596,136 | A | * | 6/1986 | Zacharias ................. 73/61.45 |
| 4,671,099 | A | * | 6/1987 | Lazarre ..................... 73/30.01 |
| 5,654,502 | A | | 8/1997 | Dutton .................... 73/152.18 |
| 5,823,262 | A | | 10/1998 | Dutton .................... 166/250.15 |
| 2002/0100505 | A1 | | 8/2002 | Keilty et al. ............. 137/487.5 |

* cited by examiner

*Primary Examiner*—Daniel S. Larkin
(74) *Attorney, Agent, or Firm*—Bacon & Thomas, PLLC

(57) ABSTRACT

The apparatus includes a sample tank for collecting and quieting a volume fraction of the fluid to be measured. The sample tank is in communication, at least at times, with a fluid containment via a filling line (L1) and a supply line (L2) connected, at least at times, with the filling line. The apparatus further includes a fluid measuring device having a vibration-type measurement pickup. A measuring tube of the measurement pickup is caused to vibrate during operation. The measuring tube is connected, at least at times, with the sample tank via a connecting line (L3), which is connected to an inlet end of the measurement pickup. The apparatus of the invention is especially suited for measuring liquids which are charged with gas and/or which tend to outgas.

41 Claims, 4 Drawing Sheets

Figure 1:
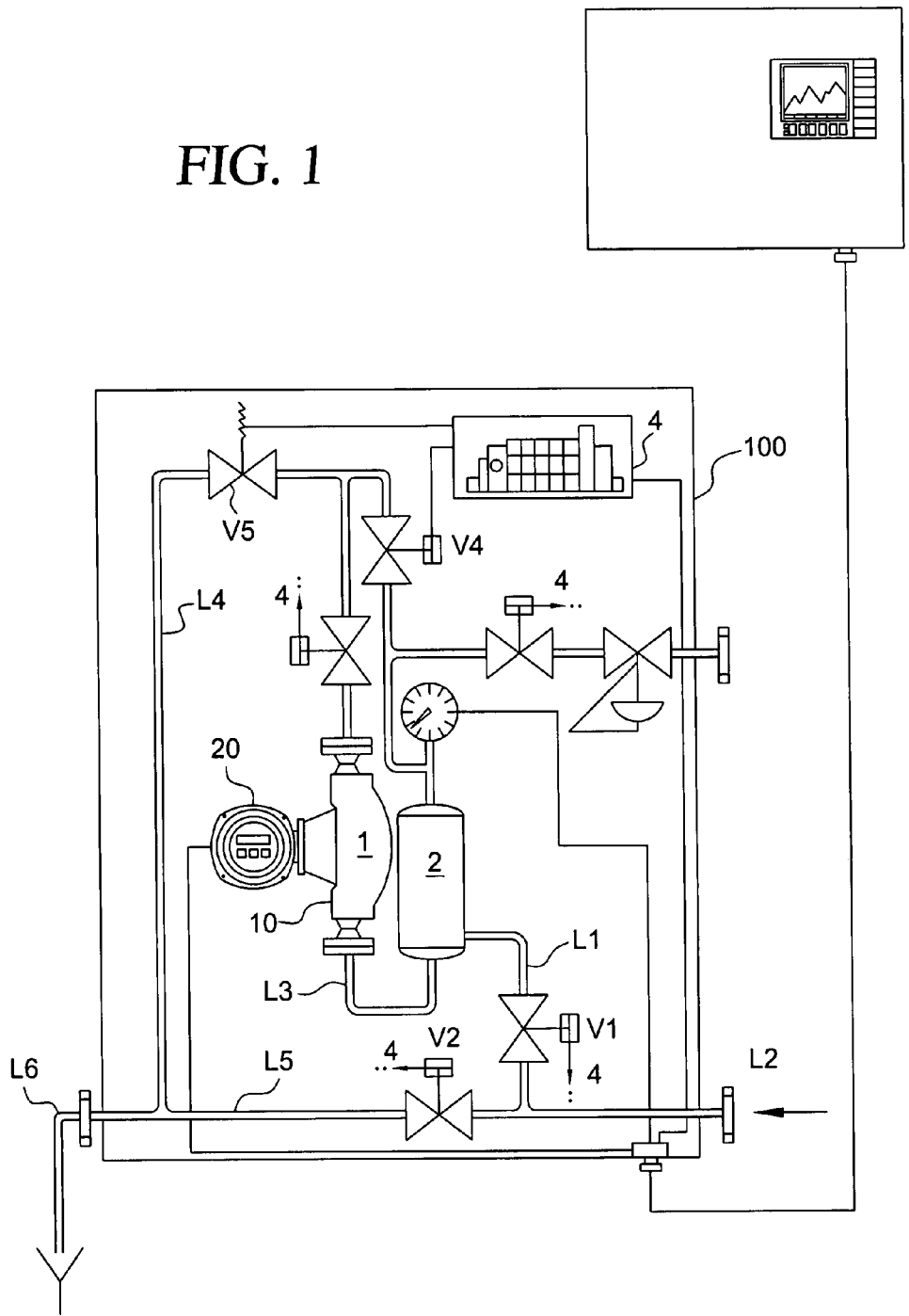

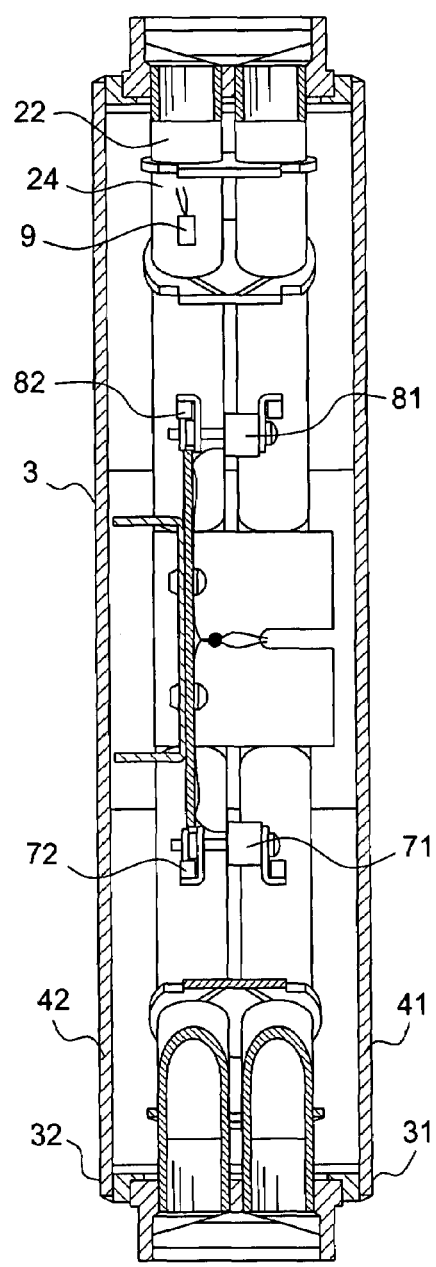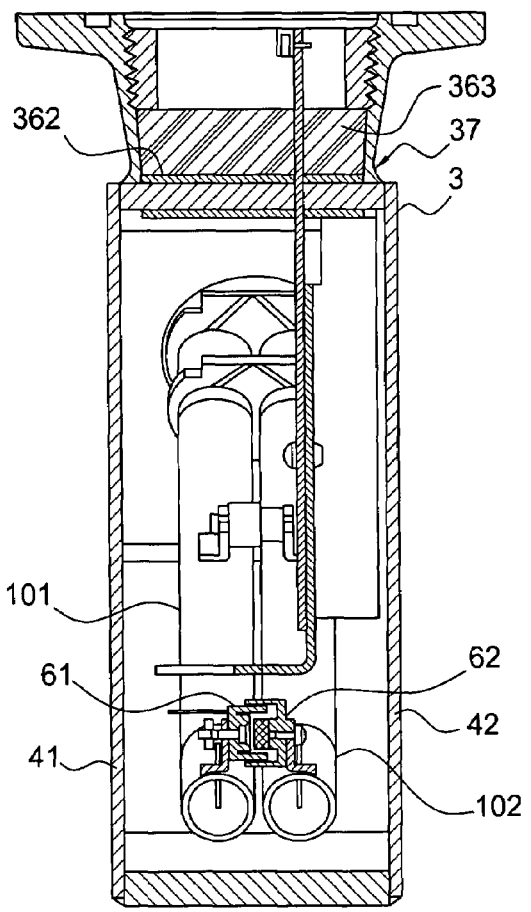
FIG. 4
FIG. 5

APPARATUS FOR MEASURING A DENSITY AND/OR A VISCOSITY OF A FLUID

FIELD OF THE INVENTION

The invention relates to an apparatus and method for measuring a density and/or a viscosity of a fluid present in a containment. Especially, the invention relates to an apparatus and method for measuring a density and/or a viscosity, in which a fluid measuring device having a vibration-type measurement pickup is used.

BACKGROUND OF THE INVENTION

In the technology of process measurements and automation, density and/or viscosity of fluids is often measured using inline measuring devices, which, by means of a vibration-type measurement pickup inserted into the course of a fluid-conveying channel and traversed by the fluid during operation, and by means of a measuring and operating circuit connected thereto, effects reaction forces in the fluid, such as e.g. inertial forces corresponding with the density or frictional forces corresponding with the viscosity, etc., and produces, derived from these forces, a measurement signal representing the respective viscosity and/or density of the fluid. Such inline measuring devices having a vibration-type measurement pickup and their manner of operation are known per se to those skilled in the art and are described in detail e.g. in WO-A 03/095950, WO-A 03/095949, WO-A 03/076880, WO-A 02/37063, WO-A 01/33174, WO-A 00/57141, WO-A 99/39164, WO-A 98/07009, WO-A 95/16897, WO-A 88/03261, U.S. 2003/0208325, U.S. Pat. No. 6,691,583, U.S. Pat. No. 6,651,513, U.S. Pat. No. 6,513,393, U.S. Pat. No. 6,505,519, U.S. Pat. No. 6,006,609, U.S. Pat. No. 5,869,770, U.S. Pat. No. 5,796,011, U.S. Pat. No. 5,602,346, U.S. Pat. No. 5,602,345, U.S. Pat. No. 5,531,126, U.S. Pat. No. 5,301,557, U.S. Pat. No. 5,253,533, U.S. Pat. No. 5,218,873, U.S. Pat. No. 5,069,074, U.S. Pat. No. 4,876,898, U.S. Pat. No. 4,733,569, U.S. Pat. No. 4,660,421, U.S. Pat. No. 4,524,610, U.S. Pat. No. 4,491,025, U.S. Pat. No. 4,187,721, EP-A 1 281 938, EP-A 1 001 254 or EP-A 553 939.

SUMMARY OF THE INVENTION

For the conveying of the medium, the measurement pickups include, in each case, at least one measuring tube held in a, for example, tubular or box-shaped, support frame. The measuring tube has a curved or straight tube segment, which is caused to vibrate, driven by an electromechanical exciter mechanism, for producing, during operation, the above-named reaction forces. For registering vibrations of the tube segment, the measurement pickups have, additionally, in each case, a physical-electrical sensor arrangement reacting to movements of the tube segment. Already the initially-referenced U.S. Pat. No. 4,524,610 and U.S. Pat. No. 4,187,721 describe how such inline measuring devices can be used to measure the instantaneous density of the flowing medium, and, indeed, on the basis of a frequency of at least one of the oscillation measurement signals delivered by the sensor arrangement. Along with the density of the fluid, such inline measuring devices with a vibration-type measurement pickup can also be used to directly measure a viscosity and/or a viscosity-density product of the fluid present in the measuring tube; compare, in this regard, especially U.S. Pat. No. 6,651,513, U.S. Pat. No. 5,531,126, U.S. Pat. No. 5,253,533, U.S. Pat. No. 4,524,610, WO-A 95/16897. Beyond these possibilities, most often also a temperature of the medium is directly measured in suitable manner, for example by means of a temperature sensor arranged on the measuring tube. It can, therefore, be presumed for the invention, without more, that, by means of modern inline measuring devices having vibration-type measurement pickups, both density, viscosity and/or temperature of the fluid can be measured; compare, in this regard, especially the already mentioned U.S. Pat. No. 6,513,393, U.S. Pat. No. 6,006,609, U.S. Pat. No. 5,602,346, WO-A 02/37063, WO-A 99/39164, or also WO-A 00/36379.

Characteristic for many physical or chemical processes, which are to be monitored with means of industrial measurement and automation technology, is that the fluids to be measured form inhomogeneous gas-liquid mixtures, e.g. by the entrainment of gases into a liquid stream or by outgassing of gases dissolved in the flowing liquid. Such commingling or segregation processes can scarcely be avoided, for example in the case of discontinuous metering- or bottling-processes or in the case of sample withdrawal from tanks or pipelines for purposes of quality monitoring.

In the use of vibration-type measurement pickups, it has been found, however, as also discussed, for example, in U.S. Pat. No. 4,524,610, that, in the case of inhomogeneous media, especially two or more phase media, the measurement signals derived from the oscillations of the measuring tube, especially also the mentioned phase-shift, display fluctuations to a considerable degree, despite the fact that viscosity and density, as well as also the concentration of the individual phases of the medium are kept practically constant and/or are appropriately taken into consideration, such that it can happen that such measurement signals can become, without compensatory measures, completely unusable for the measurement of the involved physical parameters. Examples of causes for the problems connected with the measurement of inhomogeneous fluids with vibration-type measurement pickups are unilateral attachment or deposition of gas bubbles or solid particles entrained in liquids internally on the measuring tube wall, and the so-called "bubble-effect", in which gas bubbles entrained in the liquid act as flow bodies for liquid volume portions accelerated transversely to the longitudinal axis of the measuring tube.

On the basis of these considerations, an object of the invention is to provide an apparatus which is suited for measuring the density and/or viscosity of liquid samples taken discontinuously from one or more containments. Additionally, an object of the invention is to provide a method for measuring density and/or viscosity that can be performed by means of the apparatus.

For achieving the objects, the invention concerns an apparatus for the measurement of a density and/or a viscosity of a fluid present in a containment, which apparatus includes:

a sample tank for the collecting and quieting of a volume fraction of the fluid to be measured, which tank is in communication at least at times with the containment via a filling line and a supply line connected, at least as times with the filling line; and a fluid measuring device, which includes a vibration-type measurement pickup having at least one measuring tube for conveying fluid to be measured, an exciter mechanism mechanically acting on the measuring tube for causing the measuring tube to vibrate during operation, a sensor arrangement reacting to mechanical oscillations of the measuring tube for registering vibrations of the measuring tube and for producing oscillation measurement signals representing vibrations of the measuring tube, as well as a measuring and operating electronics electrically coupled to the measurement pickup for producing an electric driving signal for the exciter mechanism and for producing at least one measured value representing the density and/or the viscosity of the fluid to be measured.

The exciter mechanism has at least one electromechanical oscillation exciter, which is coupled mechanically with the measuring tube and deforms such when activated with the driving signal. The at least one measuring tube, during operation, communicates, at least at times, with the sample tank via a connecting line, which is connected to an inlet end of the measurement pickup, and under the influence of the at least one oscillation exciter, executes, at least at times, vibrations in an oscillation mode suited for the measurement of the density and/or the viscosity. The sensor arrangement has at least one oscillation sensor, which delivers at least one, locally registered, oscillation measurement signal representing oscillations of the measuring tube.

Additionally, the invention includes a method for measuring, by means of such an apparatus, a density and/or a viscosity of a liquid located in a containment and charged with gas and/or tending to outgas, which method includes the following steps:

causing liquid taken from the containment to flow into the sample tank;

ending the flowing of liquid taken from the containment into the sample tank and permitting a liquid-gas mixture then located in the sample tank to equilibrate;

causing liquid collected in the sample tank, especially a liquid charged with a gas, to flow into the measuring tube;

registering oscillations of the measuring tube and producing at least one oscillation measurement signal representing these oscillations; and emptying the measuring tube via the drain line.

BRIEF DECRIPTION OF THE DRAWINGS

Figure 2:
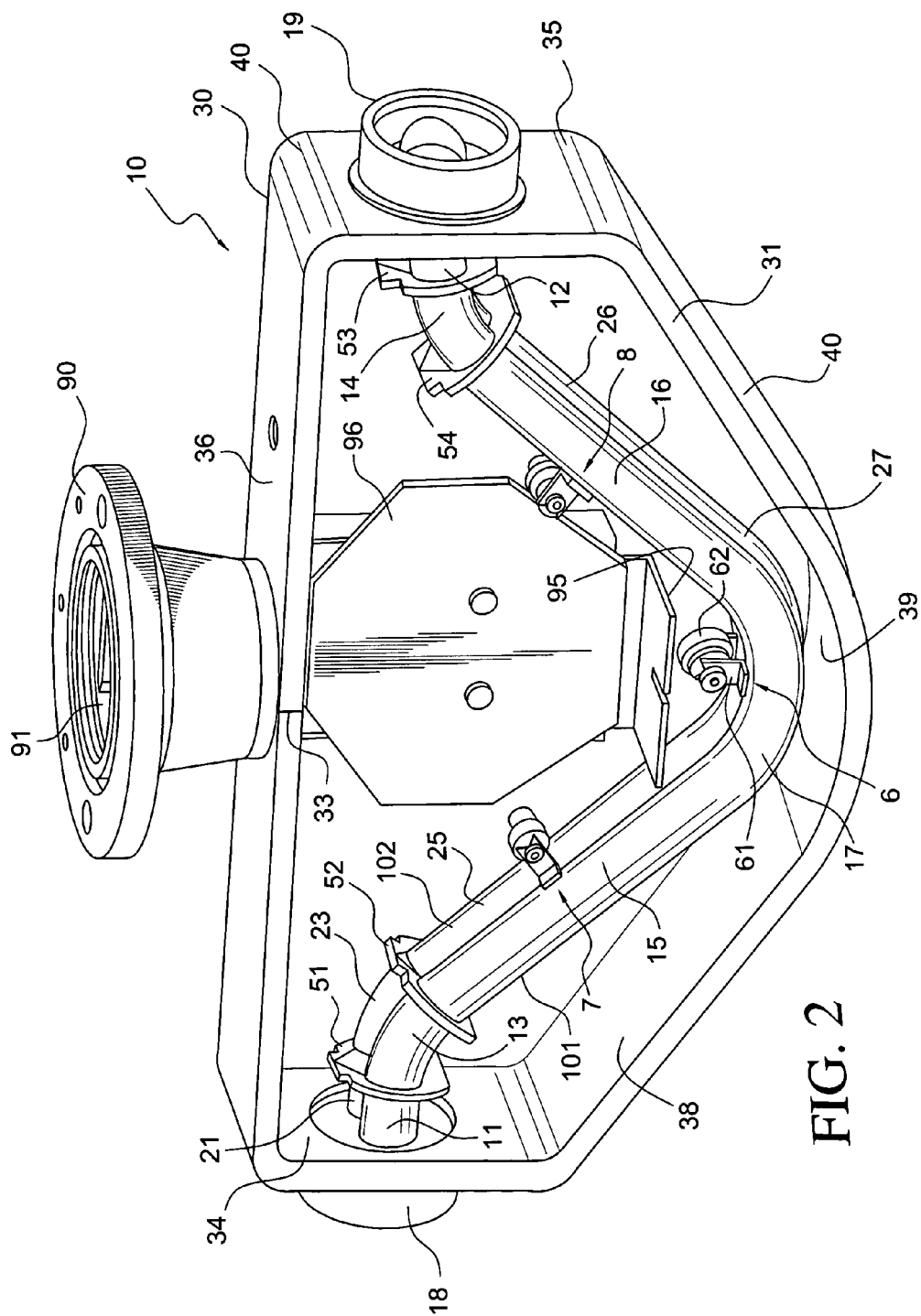
Figure 3:
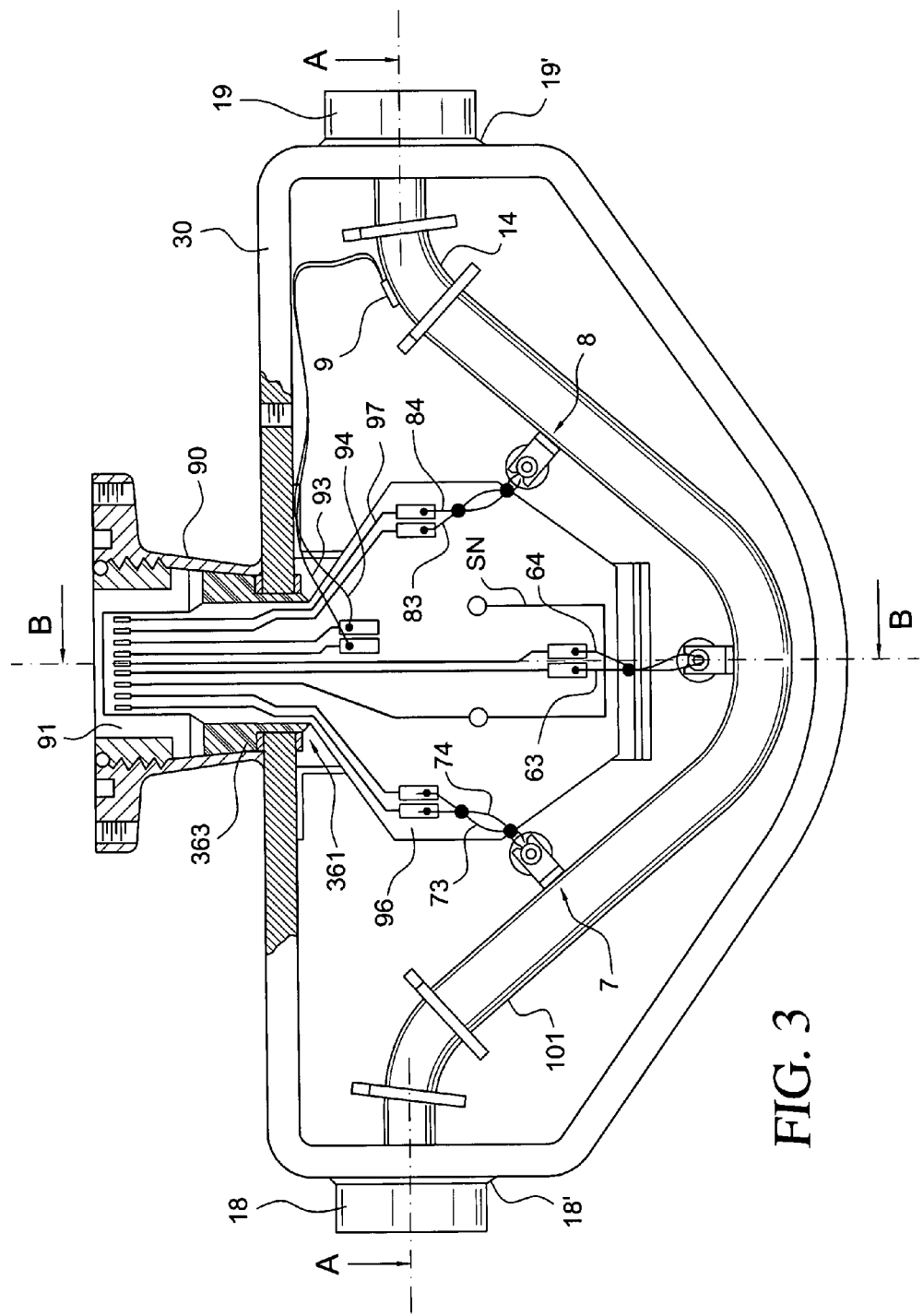

The invention will now be explained in greater detail by means of the figures of the drawing, in which a preferred example of an embodiment is presented. Functionally equal parts are provided in the individual figures with the same reference characters, but the reference characters are only repeated in subsequent figures when such appears useful. The figures of the drawing show as follows:

FIG. 1 schematically, an apparatus for measuring, by means of an inline fluid measuring device, a density and/or a viscosity of a fluid stored in a containment;

FIG. 2 perspectively, mechanical details of a vibration-type measurement pickup, minus completed housing, suitable for the inline fluid measuring device of FIG. 1;

FIG. 3 a front view of the measurement pickup of FIG. 2, again minus completed housing, however with supplemental, electrical details;

FIG. 4 a section taken on the cutting plane A-A of FIG. 3, providing a bottom view of FIG. 3, however with completed housing; and FIG. 5 a section taken on the cutting plane B-B of FIG. 3, providing a side view of FIG. 4.

DESCRIPTION OF THE PREFERRED EMBODIMENTS

In a first embodiment of the invention, the apparatus further includes a housing, in which at least the sample tank and the measurement pickup are arranged.

In a second embodiment of the apparatus of the invention, the filling line and the connecting line open separated from one another into the sample tank.

In a third embodiment of the apparatus of the invention, the sample tank has an essentially cylindrical, especially tubular, shape.

In a fourth embodiment of the apparatus of the invention, the sample tank is so arranged and oriented, that a longitudinal axis runs essentially in the direction of gravity.

In a fifth embodiment of the apparatus of the invention, the filling line opens via a side wall of the sample tank, especially in the region of a lower half of the sample tank, into the sample tank.

In a sixth embodiment of the apparatus of the invention, the at least one measuring tube communicates via an emptying line, which is connected to an outlet end of the measurement pickup, at least at times, with a collector (3) for fluid removed from the containment.

In a seventh embodiment of the invention, the apparatus further includes a bypass line, which so permits the supply line and a drain line connected, at least at times, with the emptying line to communicate with one another, such that a fluid located in the supply line can flow directly into the drain line.

In an eighth embodiment of the invention, the apparatus further includes, connected with the sample tank, at least one pressure line, which so permits the sample tank to communicate, at least at times, with a compressed gas storage and/or with a compressor, that a pressurized fluid, especially air, nitrogen or carbon dioxide, located in the pressure line can flow into the sample tank.

In a ninth embodiment of the apparatus of the invention, the emptying line communicates, at least at times, with the pressure line, so that the fluid present in the pressure line can flow into the emptying line.

In a tenth embodiment of the invention, the apparatus further includes at least one emptying shutoff valve inserted in the course of the emptying line.

In an eleventh embodiment of the invention, the apparatus further includes at least one bypass shutoff valve inserted into the course of the bypass line.

In a twelfth embodiment of the invention, the apparatus further includes at least one filling shutoff valve inserted into the course of the filling line.

In a thirteenth embodiment of the invention, the apparatus further includes at least one supply shutoff valve inserted into the course of the supply line.

In a fourteenth embodiment of the invention, the apparatus further includes at least one pressure shutoff valve inserted into the course of the pressure line.

In a fifteenth embodiment of the invention, the apparatus further includes a pressure controller inserted into the course of the pressure line.

In a sixteenth embodiment of the invention, the apparatus further includes an, especially programmable, valve control for controlling shutoff valves provided in the apparatus.

In a seventeenth embodiment of the apparatus of the invention, the measuring and operating electronics of the fluid measuring device transmits, at least at times, digitized measurement data, especially digitized measured values, to a superordinated control-and/or monitoring-unit.

In a first embodiment of the method of the invention, the step of equilibrating the liquid-gas mixture located in the sample tank includes a step of removing a gas-phase from the liquid, especially a gas-phase already present in the liquid and/or arising in the sample tank.

In a second embodiment of the method of the invention, the method further includes a step of emptying the drain line.

In a third embodiment of the method of the invention, the method further includes a step of allowing liquid to flow out of the supply line into the drain line via the bypass line.

In a fourth embodiment of the method of the invention, the step of causing liquid to flow out of the supply line into the drain line via the bypass line occurs after the step of causing liquid taken from the containment to flow into the sample tank, and the step of emptying the measuring tube via the drain line occurs after and/or during the step of causing liquid to flow from the supply line into the drain line via the bypass line.

In a fifth embodiment of the method of the invention, the step of causing liquid collected in the sample tank to flow into the measuring tube of the measurement pickup includes a step of opening the emptying shutoff valve.

In a sixth embodiment of the method of the invention, the method further includes the steps of causing liquid to flow through the measuring tube and registering oscillations of the measuring tube, as liquid is flowing through it, for producing the at least one oscillation measurement signal.

In a seventh embodiment of the method of the invention, the step of causing liquid taken from the containment to flow into the sample tank includes the step of closing the emptying shutoff valve and opening the filling shutoff valve.

In an eighth embodiment of the method of the invention, the step of equilibrating the liquid-gas mixture located in the sample tank includes the steps of closing the emptying shutoff valve, opening the pressure shutoff valve and causing a compressed gas, especially compressed air, to flow into the sample tank for altering a static, internal pressure in the sample tank.

In a ninth embodiment of the method of the invention, the step of emptying the measuring tube via the drain line includes the steps of opening the pressure shutoff valve, opening the emptying shutoff valve, and causing a compressed gas to flow into the drain line and blowing-out the same by means of the gas.

FIG. 1 shows an example of an embodiment of an apparatus for measuring a density and/or a viscosity of a fluid stored in an, especially remotely located, containment, for example a liquid-containing tank. In particular, the apparatus is suited for measuring a liquid charged with gas and/or which tends to outgas, such as e.g. beer in the process of fermentation or stored beer, milk being pasteurized, or the like.

For such purpose, the apparatus includes a sample tank 2 communicating at least at times with the containment via a supply line L2 for collecting a volume fraction of the fluid to be measured and for quieting the withdrawn fluid and/or for the equilibrating of a plurality of fluid samples taken at separated points in time from one and the same containment or from different containments. Additionally, the apparatus includes an inline fluid-measuring device 1 connected via a connecting line L3 downstream from the sample tank 2. In particular, the procedure of quieting a fluid sample, or the equilibrating of the different fluid samples in the case of a liquid-gas mixture located in the sample tank 2 is marked by the fact that a gas phase, especially a gas phase already present in the liquid and/or arising in the sample tank 2, is separated from the liquid and is allowed to accumulate above the liquid. Fluid measuring devices suited for the apparatus of the invention are described in detail, for example, in EP-A 1 291 639, U.S. Pat. No. 6,651,513, U.S. Pat. No. 6,513,393, U.S. Pat. No. 6,006,609, U.S. Pat. No. 5,687,100, U.S. Pat. No. 5,648,616, U.S. Pat. No. 5,597,949, U.S. Pat. No. 5,359,881, U.S. Pat. No. 5,317,928, U.S. Pat. No. 5,295,084, U.S. Pat. No. 4,996,871, U.S. Pat. No. 4,984,472, U.S. Pat. No. 4,876,879, U.S. Pat. No. 4,524,610, or WO-A 9516897. The fluid measuring device 1 is connected on the outlet end to an emptying line L4, which is connected, at least at times, with a drain line L6 provided externally to the apparatus.

For producing reaction forces in the fluid descriptive of the fluid, especially density-dependent, inertial forces and/or viscosity-dependent, frictional forces, the fluid measuring device includes a vibration-type measurement pickup 1 having at least one measuring tube for conveying the fluid to be measured, an exciter mechanism acting, during operation, mechanically on the measuring tube for causing the measuring tube to vibrate, as well as a sensor arrangement reacting to mechanical oscillations of the measuring tube for registering vibrations of the measuring tube and for producing oscillation measurement signals representing vibrations of the measuring tube. Vibration-type measurement pickups suited for the apparatus of the invention are detailed, for example, in U.S. Pat. No. 6,691,583, U.S. Pat. No. 6,666,098, U.S. Pat. No. 6,651,513, U.S. Pat. No. 6,308,580, U.S. Pat. No. 5,796,011, U.S. Pat. No. 5,301,557, U.S. Pat. No. 4,524,610, EP-A 1 154 243, or EP-A 685 712. The exciter mechanism of the measurement pickup is formed by at least one electromechanical oscillation exciter, which is mechanically coupled with the measuring tube and deforms such when activated by the driving signal. Additionally, the sensor arrangement is formed by at least one oscillation sensor, which delivers at least one locally registered oscillation measurement signal representing oscillations of the measuring tube. For producing a suitable electric driving signal for the exciter arrangement and for producing at least one measured value representing the density and/or the viscosity of the fluid to be measured, the fluid measuring device has, additionally, a measuring and operating electronics 20 electrically coupled to the measurement pickup. In an advantageous embodiment of the invention, it is provided that the measuring and operating electronics 20 transmits, at least at times during operation of the fluid measuring device 1, digitized measurement data, especially digitized measured values, to a superordinated control and/or monitoring unit 30.

FIG. 2 shows, perspectively, mechanical details of a vibration-type measurement pickup 10 suited for the apparatus of the invention. Such will be referred to below as measurement pickup 10, for short; for reasons of better visibility of its internal construction, the measurement pickup 10 is shown minus completed transducer housing, and FIG. 3 shows a corresponding front view with additional electrical details. In contrast, FIGS. 4 and 5 show sectional views related to FIG. 3, but, in each case, with completed transducer housing. Because of the selected presentation in the form of a perspective FIG. 2, together with the associated elevation, plan and side views of the other figures, the following explanation does not proceed figure-by-figure in the following explanation, but, instead, the figures are discussed all together.

The measurement pickup 10 has a first measuring tube 101 bent in V-shape in a first plane. Measuring tube 101 is bent symmetrically with reference to a first line of symmetry. A second measuring tube 102 bent in V-shape is bent in a second plane with reference to a second line of symmetry. The measuring tubes 101, 102 are arranged parallel to one another and each exhibits one-piece construction. The measuring tube 101 has a straight inlet piece 11 with an inlet axis lying in the first plane, a straight outlet piece 12 with an outlet axis lying in the first plane and aligning with the inlet axis; in this way, a common axis results, which is referenced in the following as inlet/outlet axis. The measuring tube 102 has a straight inlet piece 21 with an inlet axis lying in the second plane, a straight outlet piece 22 (only visible in FIG. 4) with an outlet axis lying in the first plane and aligning with the inlet axis; also this common axis is referenced in the following as inlet/outlet axis. The measuring tube 101 has, additionally, an inlet curve 13 connected with the inlet piece 11, an outlet curve 14 connected with the outlet piece 12, a first, straight, tube piece 15 connected with the inlet curve 14, a second, straight, tube piece 16 connected with the outlet curve 14, and a vertex curve 17 connected with the tube pieces 15, 16. The measuring tube 102 has, additionally, an inlet curve 23 (only visible in FIG. 2) connected with the inlet piece 21, an outlet curve 24 (only visible in FIG. 4) connected with the outlet piece 22, a first, straight tube piece 25 connected with the inlet curve 23, a second, straight, tube piece 26 connected with the outlet curve 24, and a vertex curve 27 connected with the tube pieces 25, 26. In the example of an embodiment, the bending about the axis of the vertex curve 17 and that of the vertex curve 27 essentially correspond to a circular arc. The inlet pieces 11, 21 are fixed in an inlet distributor piece 18 and the outlet pieces 12, 22 are fixed in an outlet distributor piece 19. These distributor pieces 18, 19 are held by a support frame 30, which is part of a transducer housing 3 (only visible in FIG. 4). The measuring tubes 101, 102, and the distributor pieces 18, 19 are made of stainless steel in the example of an embodiment, with the steel for the measuring tubes 101, 102, being preferably European Material No. 1.4539, which corresponds to the American designation 904 L, and that for the distributor pieces being preferably European Material No. 1.4404, which corresponds to the American designation 316 L. The use of such a double-tube arrangement formed by means of the two measuring tubes 101, 102 and the distributor pieces 18, 19 connecting them together in parallel has, it is known, among other things, the advantage that the measurement pickup is dynamically very well balanced due to the largely constant mass distribution, even in the case of significantly fluctuating fluid density. In the example of an embodiment shown here, the measuring tubes 101, 102 are connected rigidly together by means of a first node plate 51 in the vicinity of a location, at which the inlet pieces 11, 21 transition into the inlet curves 13, 23, and by means of a second node plate 52 in the vicinity of a location, at which the inlet curves 13, 23 transition into the first tube piece 15, 25. The measuring tubes 1, 2 are, additionally, connected rigidly together by means of a third node plate 53 in the vicinity of a location, at which the outlet pieces 12, 22 transition into the outlet curves 14, 24, and by means of a fourth node plate 54 in the vicinity of a location, at which the outlet curves 14, 24 transition into the second tube pieces 16, 26. The four node plates 51, 52, 53, 54 are preferably thin disks of e.g. stainless steel, especially as it is used for the transducer housing 3. These disks are provided with bores, whose outer diameters correspond to that of the measuring tubes 101, 102, and with slits, so that the disks can first be clamped on the measuring tubes 101, 102 and subsequently hard-soldered, or brazed, to them; in such case, the slits are brazed shut, so that the disks sit unslitted as node plates on the measuring tubes 101, 102.

As in the case of the measuring tubes 101, 102, the support frame 30 of the measuring pickup 10 shown in the example of an embodiment is also constructed as one piece and has been produced from a flat piece of high grade steel, e.g. a stainless steel, of constant breadth and thickness, having a front surface 31 and a rear surface 32 (only visible in FIG. 4), by appropriate bending and welding of the ends; compare the seam 33. The support frame 30 includes a planar inlet frame-piece 34, in which the inlet distributor piece 18 is welded, and a planar outlet frame-piece 35, in which the outlet distributor piece 19 is welded; compare in FIG. 3 the parts of the distributor pieces 18, 19 projecting beyond the support frame 30, with associated weld beads 18', 19'. The support frame 30 additionally includes, connecting the inlet and outlet frame-pieces 34, 35, a planar feedthrough frame-piece 36, in which an electrical feedthrough 37 (only visible in FIG. 5) is pressure-tightly secured. The feedthrough frame-piece 36 forms with the inlet and outlet frame pieces 34, 35, in each case, a right angle. The support frame includes, additionally, attached at an angle to the inlet frame-piece, a planar, first, extension frame-piece 38, with the angle of attachment being greater than 90°, in the example of an embodiment at about 120°. The support frame includes finally a curved vertex frame-piece 39 transitioning into the extension frame-piece 38 and a planar, second, extension piece 40 attached to the outlet frame-piece 35 at the named angle and transitioning into the vertex frame piece 39. The support frame 30 is completed to form the transducer housing 3 by a preferably planar, front plate 41 of stainless steel welded on the front surface 31 and a preferably planar, rear plate 42 of the same steel welded on the rear surface 32, so that it is pressure-tight. Front and rear plates 41, 42 are only visible in FIGS. 4 and 5. The steel for the transducer housing 3 of the example of an embodiment is preferably the stainless steel with the European Material No. 1.4301, which corresponds to the American designation 304.

The measurement pickup 10 is, as already mentioned, placed in the course of the tube system formed by the L3 connecting line, the emptying line L4 and, as required, the drain line L6, and flowed-through, at least temporarily, by the fluid to be measured. To this end, connection devices are provided on the inlet and outlet distributor pieces 18, 19, with examples of such connection devices being externally or internally threaded fittings, flanges or clamping devices, such as e.g. those available under the registered mark Triclamp.

An exciter mechanism 6 causes the measuring tubes 101, 102 to execute, during operation, tuning-fork-like oscillations, which usually have an oscillation frequency, which is equal to, or in the vicinity of, the mechanical resonance frequency of the oscillation system formed by the measuring tubes 101, 102. This oscillation frequency is, as is known, dependent during operation on the density of the fluid flowing through the measuring tubes 101, 102. Therefore, the density of the fluid can be determined on the basis of the oscillation frequency. A first part 61 of the exciter mechanism is affixed to the vertex curve of the measuring tube 101 in the region of its above-mentioned line of symmetry and a second part 62 of the exciter mechanism 6 is affixed to the vertex curve 27 of the measuring tube 102 in the region of its above-mentioned line of symmetry; compare FIG. 4. In the example of an embodiment shown in the figures here, the exciter mechanism 6 is an electrodynamic exciter mechanism, and, consequently, the part 61 is a coil arrangement and the part 62 a permanent magnet arrangement, which can interact with the coil arrangement by plunging. The exciter mechanism 6 is supplied from a driver circuit (not shown) with alternating current. The driver circuit can be e.g. a PLL-circuit of U.S. Pat. No. 4,801,897 always adjusting to the instantaneous resonance frequency of the oscillation system of the measuring tubes 101, 102. A first, velocity, or path, sensor 7 affixed to the measuring tubes produces an oscillation measurement signal, by means of which the density and/or the viscosity of the fluid can be determined in usual manner. In the example of an embodiment shown here, additionally, a second, velocity, or path, sensor 8 is provided, with the velocity, or path, sensors 7, 8 then being mountable, for example, symmetrically to the mentioned lines of symmetry of the measuring tubes 101, 102. This adds the advantage that, for density and/or viscosity measurement, also conventional Coriolis mass flow pickups can be used essentially unchanged and thus without expensive new design. In usual manner, a first part 71 of the velocity, or path, sensor 7 is affixed to the tube piece 15 of the measuring tube 101 and a second part 72 to the tube piece 25 of the measuring tube 102; compare FIG. 3. Equally, a first part 81 of the velocity, or path, sensor 8 is affixed to the tube piece 16 of the measuring tube 101 and a second part 82 to the tube piece 26 of the measuring tube 102; compare FIG. 3. The velocity, or path, sensors 7, 8 are preferably electrodynamic velocity sensors in the example of an embodiment of the figures; in this way, the parts 71, 81 are, in each case, a coil arrangement, and the parts 72, 82, in each case, a permanent magnet arrangement, which can plunge into the associated coil arrangement.

As was already briefly mentioned above, the feedthrough 37, containing a plurality of electric lines, is secured, especially inserted, pressure-tightly in the support frame 30 opposite the vertex curves 17, 27 and thus also opposite the vertex frame piece 39. To this end, a flange 90 is secured to the support frame 30; preferably, the flange 90 is welded to the support frame 30. The flange 90 has a bore 91, so that the feedthrough 37 is accessible from outside of the transducer housing 3. Feedthrough 37 includes a circuit board 96 secured to the support frame by means of an angled support plate 95 and extending between the support frame and the vertex curves, extending toward the vertex curves. On the circuit board are conductive traces (compare the conductive trace 97), which are only visible in FIG. 3. Connected to these conductive traces are the electric connecting lines 63, 64 of the exciter mechanism 6, the connecting lines 73, 74 of the velocity sensor 7, the connecting lines 83, 84 of the velocity sensor 8 and the connecting lines 93, 94 of a temperature sensor 9, so that these are also connected to the separate conductors of the feedthrough 37. The connecting lines 63, 64, 73, 74, 83, 84, 93, 94 are only visible in FIG. 3. Additionally, a conductive trace SN is also provided for a circuit zero point (circuit ground). Conductive trace SN is affixed, via metal securing means connected mechanically, and, therefore, also electrically, to the metal support plate 95.

Temperature sensor 9 (only visible in FIGS. 3 and 4) is secured in the illustrated example of an embodiment on the outlet piece 22 of the measuring tube 102, e.g. by adhesive, and is preferably a platinum resistor. It serves, as mentioned at the beginning, for measuring the instantaneous temperature of the fluid. Temperature sensor 9 can also be located at any other suitable location of the measuring tubes 101, 102. The feedthrough 37 includes, additionally, a slot 361 in the feedthrough frame-piece 36. Circuit board 96 extends through slot 361, into the flange 90, with sufficient separation being maintained between circuit board 96 and slot 361 to assure electrical isolation of the circuit board. Additionally, circuit board 96 extends through a disk 362 of insulating material lying on the bore-side of the feedthrough frame-piece. An insulating pottant 363 completely fills a part of the bore 91 lying above the disk 362, with the pottant 363 also penetrating more or less into the space between the circuit board 96 and the inner wall of the slot 361. The thickness of the pottant 363 in the direction toward the open end of the bore 91 is at least equal to the length of gap length prescribed for the ignition protection type Ex-d of the European Standards EN 50 014 and EN 50 018, as a function of gap width. Comparable standards of other countries correspond to these standards. Since the measurement pickup 10, as already mentioned, is to be connected with the associated measuring and operating electronics, so that a functioning fluid measuring device is obtained, an electronics housing (not shown) for the measuring and operating electronics or a connection arrangement (not shown) for a cable, which leads to an electronics housing for the measuring and operating electronics arranged remotely from the measurement pickup, is screwed into the flange 90.

During operation, especially, however, during measurement of the density and/or viscosity of the fluid, the at least one measuring tube 101 is in communication, at least at times, with the sample tank 2 via a corresponding connecting line L3, which is connected to an inlet end of the measurement pickup. Additionally, the at least one measuring tube 101 executes, during operation under the influence of the at least one oscillation exciter, vibrations, at least at times, in an oscillation mode suited for the measuring of density and/or viscosity. Oscillation modes suited for the density measurement are, for example, such, in which the measuring tube executes, at least in part, bending oscillations at a natural bending resonance frequency. In contrast, for the measurement of viscosity, those oscillation modes are especially suited, in which the measuring tube executes, at least in part, torsional oscillations having a natural torsion resonance frequency; alternatively or supplementally, however, bending oscillations can also be excited for the measurement of viscosity; compare, in this connection, also the initially mentioned U.S. Pat. No. 6,651,513.

In an additional development of the invention, the apparatus further includes, as indicated schematically in FIG. 1, a bypass line L5, which, at least at times, places the supply line L2 and the drain line L6 so in communication with one another, that a fluid present in the supply line can flow directly into the drain line. For time-dependent communicating of the supply line with the drain line, at least one bypass, shut-off valve V2 is additionally provided in the course of the bypass line L5. Furthermore, the apparatus includes, in this further development, a fill line L1, in the form of a branch line, which is connected to the bypass line L5 and to the supply line L2, and communicates via the sample tank 2, at least at times, with the supply line and/or at least at times, with the bypass line.

For measuring the density and/or the viscosity of the fluid, especially in the form of liquid, first a volume fraction thereof is taken from the containment and allowed to flow into the sample tank. After sufficient fluid has accumulated in the sample tank, the sample taking is discontinued. Then, a liquid-gas mixture located in the sample tank is allowed to age for a predetermined amount of time, in order to achieve an equilibration of the fluid, especially a separating of various phases of the mixture. After elapse of the predetermined amount of time, at least a part of the fluid collected in the sample tank is caused to flow into the at least one measuring tube 101 of the measurement pickup. For determining a measurement signal suitably representing the density and/or the viscosity, the measuring tube 101, filled with the fluid to be measured, is caused to oscillate, driven by the exciter mechanism, in the above-described manner, especially in the oscillation mode suited, in each case, for the density measurement and/or the viscosity measurement. Serving as measurement signal, in such case, is the oscillation measurement signal produced by the at least one velocity, or path, sensor 7 representing the oscillations of the two measuring tubes 101, 102 registered, here, on the inlet side. In an embodiment of the invention, the registering of oscillations of the measuring tube, as well as also the production of the at least one oscillation measurement signal occurs while the measuring tube has the fluid to be measured flowing through it.

Determination of density and/or viscosity using one or more of such oscillation measuring signals representing oscillations of the vibrating measuring tube is known, per se, to those skilled in the art and, therefore, does not require any extensive explanations here. In terms of examples, reference, in this regard, is made again to EP-A 1 291 639, U.S. Pat. No. 6,651,513, U.S. Pat. No. 6,513,393, U.S. Pat. No. 6,006,609, U.S. Pat. No. 5,687,100, U.S. Pat. No. 5,648,616, U.S. Pat. No. 5,597,949, U.S. Pat. No. 5,359,881, U.S. Pat. No. 5,317,928, U.S. Pat. No. 5,295,084, U.S. Pat. No. 4,996,871, U.S. Pat. No. 4,984,472, U.S. Pat. No. 4,876,879, U.S. Pat. No. 4,524,610, or WO-A 9516897. At the latest, after the density and/or viscosity of the fluid has been determined, the at least one measuring tube 101 is emptied via the emptying line and the drain line, at least at times, in communication therewith. The drain line is connected to an outline line of the measurement pickup 10.

In an embodiment of the invention, the sample tank has an essentially cylindrical, especially tubular, shape. In this way, the sample tank can be constructed advantageously by means of available, standard fluid containments. Preferably, the, especially cylindrical, sample tank is so arranged and oriented in the apparatus, that a longitudinal axis extends essentially in the direction of gravity. Therefore, a volume especially suited for the quieting and/or stabilization of the fluid is provided. If required, the sample tank can also be so arranged in the apparatus, that the longitudinal axis has an angle measured from the direction of gravity which is different from zero, for example smaller than or equal to 45°, whereby especially the flow-in behavior of the fluid into the sample tank can be optimized.

In a further embodiment of the apparatus of the invention, the supply line or, as shown in FIG. 1, the filling line L1, and the connecting line L3, open into the sample tank 2 at separated locations. For example, the filling line L1, as shown schematically in FIG. 1, can open into the sample tank via a side wall of the sample tank, while the connecting line L3 opens into a floor of the sample tank. Advantageously, in such case, also the opening of the supply line is placed in the area of a lower half of the sample tank. Due to the separation of the openings of filling line L1 and connecting line L3, opening shapes optimum for flow-in and for flow-out can be used. For example, flow-in angles suited for the fluid to be measured and for the shape of the containment can be selected with reference to the side wall for the fluid flowing-in via the filling line, in order to achieve an optimization of the fluid flow. For controlling the flow of the fluid into the at least one measuring tube 101, additionally provided in the apparatus is a corresponding filling shutoff valve V1, which is inserted at least in the course of the filling line. In addition, a corresponding supply shutoff valve can be placed into the course of the supply line, if necessary.

In a further development of the invention, the at least one measuring tube 101 communicates via an emptying line L4, which, as schematically illustrated in FIG. 1, is connected to an outlet end of the measurement pickup 10, at least at times, with an, especially central, collector 3 for fluid removed from the containment, for example a waste water tank, a drainage conduit or a drainage channel, so that the measuring tube 101, along with the emptying line and the drain line, can be emptied into the collector.

For the temporary closing of the emptying line, additionally at least one drain shutoff valve V5 inserted in the course of the drain line is provided. In an embodiment of this further development of the invention, the emptying shutoff valve V5 is first opened, at least for a time, to permit flow into the measuring tube 101 of fluid collected in the sample tank 2. For example, this permits the measurement also in the case of fluid flowing, especially steady state, in the measuring tube 101.

In an embodiment of this further development of the invention, it is further provided that a filling shutoff valve V1 is inserted into the course of the filling line L1. To permit fluid removed from the containment to flow into the sample tank 2, the filling shutoff valve V1 is correspondingly opened, while, in contrast, the emptying shutoff valve V5 is closed during this procedure, or at least will be closed; if necessary, the emptying shutoff valve V5 can be opened for a short time during the causing of the fluid to flow into the sample tank, so that the fluid can also already flow into the measuring tube 101. This has, for example, the advantage that the temperature sensor 9 provided in the measurement pickup 10 can be used for determining the instantaneous fluid temperature, which, in turn, can serve for determining an optimum amount of time for the quieting of the fluid in the sample tank. For quieting the fluid present in the sample tank, especially fluid in the form of a liquid-gas mixture, the emptying shutoff valve V4 is subsequently closed.

In another embodiment of the invention, it is provided that the fluid from the supply line is allowed to flow via bypass line L5, with simultaneously closed filling line L1, directly into the drain line. This has the advantage that at least the supply line L2 connecting the containment and the apparatus can be rinsed by means of the momentarily flowing fluid, while, in parallel therewith, also a measurement of fluid introduced in the meantime into the measuring tube 101 can occur. To this end, it is provided that the step of causing fluid to flow from the supply line L2 into the drain line L6 via bypass line L5 occurs only after the step of causing liquid removed from the containment to flow into the sample tank 2. Moreover, it is, therefore, not absolutely required that the measuring tube 101 only be emptied after the bypass line L5 has been emptied. Rather, this can also occur, in advantageous manner, while fluid is being allowed to flow from the supply line L2 via the bypass line L5 into the drain line L6. In a further embodiment, the fluid momentarily flowing through the bypass line is that which is to be measured in a subsequent measurement procedure.

In a further development of the invention, additionally connected with the sample tank is at least one pressure line, which enables the sample tank to communicate, at least at times, with a compressed gas storage unit and/or with a compressor, such that a fluid present therein, as well as in the pressure line, can be made to flow into the drain line. Additionally, also the drain line can be allowed to communicate, at least at times, with the pressure line, so that the fluid present in the pressure line can also flow into the drain line, for blowing such out. For the temporary closing of the pressure line, the apparatus includes at least one pressure shutoff valve inserted into the course of the pressure line. For emptying the measuring tube via the drain line, the pressure shutoff valve and the drain shutoff valve can be opened, for example, one after the other, so that then a compressed gas present in the pressure line is allowed to flow into and through for blowout of the sample tank, the connecting line of the at least one measuring tube, as well as also the drain line. In an embodiment of the invention, for quieting and/or equilibrating fluid collected in the sample tank, before the allowing of same to flow into the measuring tube, the pressure shutoff valve is opened, and a compressed gas, especially air, nitrogen or carbon dioxide, is allowed to flow into the sample tank, whereby a static internal pressure in the sample tank is altered, in this case increased. In an embodiment of this further development of the invention, a pressure regulator is provided, in addition to the pressure shutoff valve, or integrated therein, inserted into the course of the pressure line, for maintaining the pressure existing in the pressure line constant.

For controlling shutoff valves, especially such in the form of solenoid valves provided in the apparatus, the apparatus further includes an electronic, especially programmable, valve control unit 4, which is connected electrically, or at least by radio, with the shutoff valves.

The apparatus of the invention additionally includes, in an advantageous further development, a housing 100, in which at least the sample tank 2 and the measurement pickup 10 are arranged. In this way, the apparatus can be constructed as a single, especially mobile, compact device, which is externally essentially completely encapsulated and which thus can be utilized very universally and largely independently of the environmental conditions existing at the site. Additionally, the apparatus, embodied as a compact device, is very easy to clean and can therefore satisfy highest hygienic requirements, such as exist e.g. in the foods industry.

The invention claimed is:

1. An apparatus for the measurement of a density and/or a viscosity of a fluid present in a containment, said apparatus comprising:
   a filling line;
   a supply line;
   a connecting line;
   an emptying line:
   a pressure line;
   a sample tank for the collecting and quieting of a volume fraction of the fluid to be measured, which tank is in communication, at least at times, with the containment via said filling line and said supply line connected, at least at times, with said filling line;
   a collector for fluid removed from the containment; and
   a fluid measuring device, comprising a vibration measurement pickup and measuring and operating electronics electrically coupled to said vibration measurement pickup including at least one measuring tube for conveying fluid to be measured, said at least one measuring tube communicates, at least at times, with said sample tank via said connecting line, which is connected to an inlet end of said vibration measurement pickup, an exciter mechanism mechanically acting on said at least one measuring tube for causing said at least one measuring tube to vibrate during operation, a sensor arrangement reacting to mechanical oscillations of said at least one measuring tube for registering vibrations of said at least one measuring tube and for producing oscillation measurement signals representing vibrations of said at least one measuring tube, wherein:
   said measuring and operating electronics producing an electric driving signal for said exciter mechanism and said measuring and operating electronics producing at least one measured value representing the density and/ or the viscosity of the fluid to be measure; and
   said at least one measuring tube communicates via said emptying line, which is connected, at least at times, to an outlet end of said at least one measurement pickup, with said collector, and said emptying line communicates, at least at times, with said pressure line, so that fluid present in said pressure line can flow into said emptying line.

2. The apparatus as claimed in claim 1, further including:
   a housing, in which at least the sample tank and said vibration measurement pickup are arranged.

3. The apparatus as claimed in claim 1, wherein:
   said filling line and said connecting line open, separated from one another, into said sample tank.

4. The apparatus as claimed in claim 1, wherein:
   said sample tank has an essentially cylindrical, tubular, shape.

5. The apparatus as claimed in claim 1, wherein:
   said sample tank is so arranged and oriented, that a longitudinal axis runs essentially in the direction of gravity.

6. The apparatus as claimed in claim 1, wherein:
   said filling line opens via a side wall of said sample tank, in the region of a lower half of said sample tank, into said sample tank.

7. The apparatus as claimed in claim 1, wherein:
   said exciter mechanism includes at least one electromechanical oscillation exciter, which is coupled mechanically with said at least one measuring tube and deforms such when activated with the driving signal; and
   said at least one measuring tube under the influence of said at least one electromechanical oscillation exciter, executes, at least at times, vibrations in an oscillation mode suited for the measurement of the density and/or the viscosity.

8. The apparatus as claimed in claim 7, further including:
   a bypass line; and
   a drain line, wherein:
   said bypass line permits said supply line and said drain line, at least at times, with said emptying line to communicate with one another, such that a fluid located in said supply line can flow directly into said drain line.

9. The apparatus as claimed in claim 8, further including:
   at least one bypass shutoff valve inserted into said bypass line.

10. The apparatus as claimed in claim 7, wherein:
    said sensor arrangement includes at least one oscillation sensor, which delivers at least one, locally registered, oscillation measurement signal representing oscillations of said at least one measuring tube.

11. The apparatus as claimed in claim 7 further including:
    at least one emptying shutoff valve inserted into said emptying line.

12. The apparatus as claimed in claim 11, further including:
    at least one pressure shutoff valve inserted into said pressure line.

13. The apparatus as claimed in claim 11, further including:
    a pressure controller inserted into said pressure line.

14. The apparatus as claimed in claim 1, further including:
    at least one pressure line connected with said sample tank, thus permitting said sample tank to communicate, at least at times, with a compressed gas storage and/or with a compressor, so that a pressurized fluid, located in said pressure line can flow into said sample tank.

15. The apparatus as claimed in claim 1, further including:
at least one filling shutoff valve inserted into said filling line.

16. The apparatus as claimed in claim 1, further including:
at least one supply shutoff valve inserted into said supply line.

17. The apparatus as claimed in claim 1, further including:
a programmable, valve control for controlling shutoff valves provided in the apparatus.

18. The apparatus as claimed in claim 1, further including:
a superordinated control and/or monitoring unit, wherein:
said measuring and operating electronics of the fluid measuring device transmits, at least at times, digitized measurement data, to said superordinated control and/or monitoring unit.

19. The apparatus as claimed in claim 1, used for:
measuring a density and/or a viscosity of a fluid present in a containment.

20. The apparatus as claimed in claim 1, wherein:
the apparatus is constructed as a compact device.

21. The apparatus as claimed in claim 20, wherein:
the apparatus is constructed as a mobile device.

22. The apparatus as claimed in claim 1 used for:
measuring a density and/or a viscosity of a liquid charged with gas and/or tending to outgas.

23. The apparatus as claimed in claim 1 used for:
measuring a density and/or a viscosity of beer.

24. A method for measuring a density and/or a viscosity of a liquid located in a containment and charged with gas and/or tending to outgas, by means of an apparatus as claimed in claim 8, said method comprises the following steps:
causing liquid taken from the containment to flow into the sample tank;
ending the flowing of liquid taken from the containment into the sample tank and permitting a liquid-gas mixture then located in the sample tank to equilibrate;
causing liquid collected in the sample tank, to flow into the measuring tube;
registering oscillations of the measuring tube and producing at least one oscillation measurement signal representing these oscillations; and
emptying the measuring tube via the drain line.

25. The method as claimed in claim 24, wherein:
the step of equilibrating the liquid-gas mixture located in the sample tank comprises a step of removing a gas-phase from the liquid.

26. The method as claimed in claim 24, further comprising the step of:
emptying the drain line.

27. The method as claimed in claim 24, further comprising a step of:
causing liquid to flow out of the supply line into said drain line via the bypass line.

28. The method as claimed in claim 27, wherein:
said step of causing liquid to flow out of the supply line into the drain line via the bypass line occurs after the step of causing liquid taken from the containment to flow into the sample tank; and
said step of emptying the measuring tube via the drain line occurs after and/or during the step of causing liquid to flow from the supply line into the drain line via the bypass line.

29. The method as claimed in claim 24, wherein
the apparatus further comprises at least one emptying shutoff valve inserted into the emptying line, and wherein:
said step of causing liquid collected in the sample tank to flow into the measuring tube of the measurement pickup includes a step of opening the emptying shutoff valve.

30. The method as claimed in claim 29, wherein,
the apparatus further comprises at least the supply shutoff valve inserted into the supply line, and wherein:
said step of causing liquid taken from the containment to flow into the sample tank includes the following steps: closing the emptying shutoff valve; and opening the filling shutoff valve.

31. The method as claimed in claim 30, wherein
the apparatus further comprises at least one pressure shutoff valve inserted into the pressure line, and wherein:
said step of equilibrating the liquid-gas mixture located in the sample tank includes the following steps: closing the emptying shutoff valve, opening the pressure shutoff valve; and causing a compressed gas, to flow into the sample tank for altering a static, internal pressure in the sample tank.

32. The method as claimed in claim 24, further comprising the steps of:
causing liquid to flow through the measuring tube; and
registering oscillations of the measuring tube, as liquid is flowing through it, for producing the at least one oscillation measurement signal.

33. The method as claimed in claim 24, wherein
the apparatus further comprises at least one emptying shutoff valve inserted into the emptying line, and at least one pressure shutoff valve inserted into the pressure line, and wherein:
said step of emptying the measuring tube via the drain line includes the following steps: opening the pressure shutoff valve; opening the emptying shutoff valve; and causing a compressed gas to flow into the drain line and blowing-out the drain line by means of the gas.

34. An apparatus for the measurement of a density and/or a viscosity of a fluid present in a containment, said apparatus comprising:
a housing;
a filling line;
a supply line;
a connecting line;
a sample tank for the collecting and quieting of a volume fraction of the fluid to be measured, which tank is in communication, at least at times, with the containment via said filling line and said supply line connected, at least at times, with said filling line;
a collector for fluid removed from the containment; and
a fluid measuring device comprising a vibration measurement pickup and measuring and operating electronics electrically coupled to said vibration measurement pickup, said vibration measurement pickup including:
at least one measuring tube for conveying fluid to be measured, said at least one measuring tube communicates, at least at times, with the sample tank via said connecting line, which is connected to an inlet end of said vibration measurement pickup;
an exciter mechanism mechanically acting on said at least one measuring tube for causing said at least one measuring tube to vibrate during operation; and
a sensor arrangement reacting to mechanical oscillations of said at least one measuring tube for registering vibrations of said at least one measuring tube and for producing oscillation measurement signals representing vibrations of said at least one measuring tube;

said measuring and operating electronics producing an electric driving signal for said exciter mechanism and said measuring and operating electronics producing at least one measured value representing the density and/or the viscosity of the fluid to be measured, wherein:
said sample tank and said vibration measurement pickup are arranged within said housing.

35. The apparatus as claimed in claim 34, wherein:
said filling line and said connecting line open, separated from one another, into said sample tank.

36. The apparatus as claimed in claim 34, further including:
a collector; and
an emptying line, wherein:
said at least one measuring tube communicates via said emptying line, which is connected, at least at times, to an outlet end of said at least one measurement pickup, with said collector for fluid removed from the containment.

37. The apparatus as claimed in claim 36, further including:
a bypass line, and a drain line, wherein: said bypass line permits said supply line and said drain line, at least at times, with said emptying line to communicate with one another, that a fluid located in said supply line can flow directly into said drain line.

38. The apparatus as claimed in claim 34, wherein:
the apparatus is constructed as a compact device.

39. The apparatus as claimed in claim 38, wherein:
the apparatus is constructed as a mobile device.

40. The apparatus as claimed in claim 34 used for:
measuring a density and/or a viscosity of a liquid charged with gas and/or tending to outgas.

41. The apparatus as claimed in claim 34 used for:
measuring of beer.

\* \* \* \* \*